United States Patent [19]

Herve et al.

[11] Patent Number: 4,824,673

[45] Date of Patent: Apr. 25, 1989

[54] NEW DRUGS BASED ON EXTRACTS OF ALGAE, AND CORRESPONDING FORMULATIONS

[75] Inventors: René Herve, Pludono; Serge Percehais, Saint-Malo, both of France

[73] Assignee: Goemar S.A., France

[21] Appl. No.: 559,849

[22] Filed: Dec. 9, 1983

Related U.S. Application Data

[63] Continuation of Ser. No. 419,170, Sep. 17, 1982, abandoned.

[30] Foreign Application Priority Data

Sep. 23, 1981 [FR] France ................. 81 17943

[51] Int. Cl.$^4$ ............................................. A61K 35/78
[52] U.S. Cl. .................................................. 421/195.1
[58] Field of Search ............... 424/195, 195.1, 140, 424/145, 154

[56] References Cited

U.S. PATENT DOCUMENTS 4,023,734  5/1977  Hervé et al. ................. 241/17

FOREIGN PATENT DOCUMENTS 693024  7/1967  Belgium .
1485766  6/1967  France .
5576M   1/1968  France .
2242991 9/1973  France .

*Primary Examiner*—John W. Rollins
*Attorney, Agent, or Firm*—Marshall & Melhorn

[57] ABSTRACT

New drugs consisting of protoexoplasma of red or brown algae.

Said protoexoplasma is a product obtained by subjecting the algae to a special treatment including in particular a cryogrinding. The combination of this product with oligo-elements promotes the assimilation of the latter.

10 Claims, No Drawings

NEW DRUGS BASED ON EXTRACTS OF ALGAE, AND CORRESPONDING FORMULATIONS

This application is a continuation of application Ser. No. 419,170, filed 9-17-82, now abandoned.

The present invention relates to the use in therapeutics of especially prepared extracts of certain algae.

Several families of algae are known to exist.

The algae used according to the present invention belong to the family of the brown algae (or Phaeophyceae) or of the red algae (or Rodophyceae).

The invention more particularly relates to the discovery of unexpected properties in the following algae:
brown algae:
  Bifurcaria Rotunda
  Fucus Vesiculosus
  Ascophyllum Nodosum
  Pelvetia Canaliculata
red algae:
  Delesseria Sanguinea.

The properties discovered according to the invention are closely related to the special treatment of these algae which leads to a product presenting special physico-chemical characteristics:

The algae are treated as follows:

The algae are collected, and then washed in a pool in order to remove all traces of animalcules and sand.

The algae are thereafter deep-frozen, namely in a plate-type freezer, to $-10°/-30°$ C., in order to preserve the useful elements.

Then they are placed in cold storage for general preservation due to the fact that the crops are seasonal.

The algae are thereafter subjected to a cryogrinding (using for example two grinders in series under liquid nitrogen) and then to a rolling operation (with, for example, a cylinder machine) and finally to a homogenization. A "mother pulp" is thus obtained of which the constituent particles are approximately between 6 and 20 $\mu$. Said mother pulp is also called "algae cream".

The said mother pulp can be caused to pass over a decanter at high speed, giving thus two products, on the one hand, the solid part or cake which is called "algae base" and, on the other, the decanted liquid or juice which is called "protoexoplasma of algae".

Alternatively by way of indication, the said mother pulp can also be used as is.

Also, by way of indication, it is possible to carry out a lyophilization of both the algae cream and protoexoplasma, to obtain a dry form to be subsequently used for producing tablets and the like, for example.

The aforesaid succession of operation is of course applicable to each variety of algae.

To prepare the different extracts, useful reference can be made to French Pat. No. 74/35162 filed on Oct. 18, 1974 in the names of HERVE and ROULLIER.

The cake of algae can be used for example for producing soaps and the like, since it contains 4 to 6% cellulose, 38 to 40% insoluble alginates, as well as liposoluble vitamins.

But the object of the invention is the use for the afresaid purpose of the "protoexoplasma" of algae.

The test which have been conducted have revealed the fact that these products form a vehicle which promotes the assimilation of oligo-elements such as Cu, Mg, Mn and the like.

It is thus the aim of the present invention to combine a protoexoplasma of Rodophyceae or of Phaeophyceae with oligo-elements, such combination having the unexpected property of considerably promoting the assimilation of the oligo-elements. This protoexoplasma was obtained according to the following method. The brown algae, Ascophyllum Nodosum, were collected, then washed in a pool of sea water to remove all traces of animalcules and sand.

These algae were thereafter deep-frozen in a plate type freezer to $-15°$ C. Then they were placed in cold storage at $-25°$ C. in order to preserve all the useful elements. The algae were subjected to a cyrogrinding by passage through a tower with injection of liquid nitrogen at $-50°$ C. They were then micro-ground by being sent through 2 cellular grinders cooled from the inside by way of a cooling agent to a temperature below $-20°$ C. The resulting cream was then being homogenized in a tank at room temperature.

The mother pulp thus obtained was thereafter caused to pass over a high speed decanter, and the decanted liquor was collected; this liquor being the protoexoplasma; this protoexoplasma has the aspect of a greenish liquid, of density slightly greater than 1.

Test have been conducted on a patient. The administration of protoexoplasma on its own has produced no increase of the level of magnesium in the blood. But, an oral administration twice daily for one month of 5 ml of a combination of protoexoplasma of Ascophyllum Nodosum with the usual concentration (30–100 mg of Mg cations per dose) in Mg oligo-element has produced, on the contrary, an increase from 20 to 25% of the level of magnesium in the blood after a month.

A one-month interruption of the treatment caused a return to the initial level of 20%.

Another one-month treatment brought back the magnesium level of magnesium in the blood up to 25%.

Thus a higher assimilation was noted, where the magnesium is concerned, than with the conventionally known drugs.

Substantially the same results were obtained with copper. (12–13 $\mu$moles/1″14 $\mu$moles/1).

The new drugs according to the invention are therefore useful in the aforecited conditions for treating oligo-elements deficiencies, in particular Cu and Mg, and therefore enable to prevent certain heart diseases for example, and to cure phathological conditions known of the practitioner and which are linked with such deficiencies.

What is claimed is:

1. A method for treating humans and domesticated animals to increase the level of cations in the blood, the method comprising the step of:
   administering orally a composition consisting essentially of protoexoplasma of brown or red algae containing a cation that is selected from a member of the group consisting of Cu, Mg, Mn and Zn, the composition being administered in such proportions that a 5ml portion of the composition contains from about 30 to 100mg of the cation.

2. A method as defined in claim 1 in which the algae is Bifurcara Rotunda.

3. A method as defined in claim 1 in which the algae is Furcus Vesiculosus.

4. A method as defined in claim 1 in which the algae is Ascophyllum Nodosum.

5. A method as defined in claim 1 in which the algae is Pelveta Canaliculata.

6. A method as defined in claim 1 in which the cation is Mg and the increase in the level of Mg in the blood after about one month is at least about 20%.

7. A method for treating humans and domesticated animals to increase the level of cations in the blood, the method comprising the step of:
administering orally a composition consisting essentially of protoexoplasma of brown or red algae containing a cation that is selected from a member of the group consisting of Cu, Mg, Mn and Zn, the composition being administered in an effective amount to increase the level of the cation in the blood.

8. A method as defined in claim 7 in which the amount administered is equivalent to a twice daily dose of the composition in which the amount of the cation present is about 30 to 100mg per dose.

9. A method as defined in claim 7 in which the algae is brown algae.

10. A method treating humans and domesticated animals with a composition consisting essentially of protoexoplasma of Ascophyllum Nodosum and magnesium (Mg) cations, the method comprising the step of:
administering orally the composition to humans and domesticated animals in an effective amount, equivalent to a dose of 30 to 100mg of Mg twice daily, to raise the level of Mg in the blood at least about 20% after a month.

* * * * *